United States Patent
Cerrone et al.

(10) Patent No.: US 11,243,168 B2
(45) Date of Patent: Feb. 8, 2022

(54) SYSTEM AND A METHOD FOR ANALYSIS OF VENT GAS OF A UREA PLANT

(71) Applicant: SAIPEM S.p.A., San Donato Milanese (IT)

(72) Inventors: Cristina Cerrone, San Donato Milanese (IT); Lino Carlessi, Dalmine (IT); Alberto Serrafero, San Donato Milanese (IT); Francesco Viola, San Donato Milanese (IT)

(73) Assignee: SAIPEM S.P.A., San Donato Milanese (IT)

( * ) Notice: Subject to any disclaimer, the term of this patent is extended or adjusted under 35 U.S.C. 154(b) by 40 days.

(21) Appl. No.: 16/330,986

(22) PCT Filed: Sep. 19, 2017

(86) PCT No.: PCT/IB2017/055658
§ 371 (c)(1),
(2) Date: Mar. 6, 2019

(87) PCT Pub. No.: WO2018/051313
PCT Pub. Date: Mar. 22, 2018

(65) Prior Publication Data
US 2019/0257744 A1    Aug. 22, 2019

(30) Foreign Application Priority Data
Sep. 19, 2016    (IT) .................. 102016000093986

(51) Int. Cl.
*G01N 21/65*    (2006.01)
*G01N 1/22*    (2006.01)
(Continued)

(52) U.S. Cl.
CPC ........... *G01N 21/65* (2013.01); *C07C 273/04* (2013.01); *G01N 1/2247* (2013.01); *G01N 21/15* (2013.01);
(Continued)

(58) Field of Classification Search
CPC ............... G01N 21/65; G01N 1/10; G01N 1/22; G01N 1/2247; G01N 2001/105;
(Continued)

(56) References Cited

U.S. PATENT DOCUMENTS

| 3,451,895 A | 6/1969 | Webb |
| 5,233,996 A * | 8/1993 | Coleman ................ A61B 5/083 128/205.12 |

(Continued)

FOREIGN PATENT DOCUMENTS

| CN | 1685217 A | 10/2005 |
| CN | 101393120 A | 3/2009 |

(Continued)

OTHER PUBLICATIONS

Notification Concerning Submission, Obtention or Transmittal of Priority Document for International Application No. PCT/IB2017/055658 dated Nov. 22, 2017.

(Continued)

*Primary Examiner* — Violeta A Prieto
(74) *Attorney, Agent, or Firm* — Neal, Gerber & Eisenberg LLP

(57) ABSTRACT

A system for analysis of vent gas of a urea plant, comprising: a Raman spectroscope; a sampling conduit that connects the spectroscope to a main pipe of the urea plant configured to convey a sample stream to be analysed to the spectroscope; and a temperature-adjusting device, operated by a temperature controller and acting on at least one thermal treatment (Continued)

portion of the conduit configured to adjust the temperature of the sample stream circulating in the conduit.

16 Claims, 2 Drawing Sheets

(51) Int. Cl.
| | |
|---|---|
| *G01N 21/15* | (2006.01) |
| *G01N 21/85* | (2006.01) |
| *G01N 21/01* | (2006.01) |
| *G01N 1/10* | (2006.01) |
| *C07C 273/04* | (2006.01) |

(52) U.S. Cl.
CPC ....... *G01N 21/85* (2013.01); *G01N 2001/105* (2013.01); *G01N 2001/2282* (2013.01); *G01N 2021/0193* (2013.01); *G01N 2021/158* (2013.01); *G01N 2021/651* (2013.01); *G01N 2021/8578* (2013.01); *Y02P 20/582* (2015.11)

(58) Field of Classification Search
CPC ... G01N 2001/2282; G01N 2021/0193; G01N 2021/158; G01N 2021/8578; G01N 21/15; G01N 21/85; Y02P 20/582; Y02P 20/141; Y02P 20/142; C07C 273/04
See application file for complete search history.

(56) References Cited

U.S. PATENT DOCUMENTS

| | | | |
|---|---|---|---|
| 5,637,809 A | 6/1997 | Traina et al. | |
| 5,807,750 A | 9/1998 | Baum et al. | |
| 10,209,191 B2 * | 2/2019 | Rugnone | ................ G01N 21/65 |
| 2004/0233425 A1 * | 11/2004 | Long | ....................... C08F 10/00 |
| | | | 356/301 |
| 2012/0282149 A1 * | 11/2012 | Mennen | ................ C07C 273/04 |
| | | | 422/187 |
| 2015/0107333 A1 * | 4/2015 | Thompson | ............. G01N 30/88 |
| | | | 73/23.41 |
| 2015/0377750 A1 | 12/2015 | Scipolo et al. | |
| 2017/0102333 A1 * | 4/2017 | Rugnone | ................ C07C 273/04 |
| 2019/0170648 A1 * | 6/2019 | Slater | ..................... G01N 21/35 |
| 2020/0363339 A1 * | 11/2020 | Slater | ..................... G01N 21/65 |

FOREIGN PATENT DOCUMENTS

| | | |
|---|---|---|
| CN | 204439561 U | 7/2015 |
| DE | 41 09 688 | 10/1992 |
| EP | 1 398 617 | 3/2004 |
| EP | 2693198 A2 | 2/2014 |
| EP | 2 955 506 | 12/2015 |

OTHER PUBLICATIONS

International Search Report and Written Opinion for International Application No. PCT/IB2017/055658 dated Jan. 15, 2018.
PCT Demand for International Preliminary Examination and Reply to International Search Report and the associated Written Opinion for International Application No. PCT/IB2017/055658 dated Jul. 19, 2018.
Notification of Receipt of Demand by Competent International Preliminary Examining Authority (Form PCT/IPEA/402) for International Application No. PCT/IB2017/055658 dated Aug. 21, 2018.
Notification of Transmittal of the International Preliminary Report on Patentability (Form PCT/IPEA/416) for International Application No. PCT/IB2017/055658 dated Sep. 24, 2018.
Chinese Office Action and Search Report for Application No. 201780054381.3 dated Dec. 2, 2020 (7 pages).

* cited by examiner

SYSTEM AND A METHOD FOR ANALYSIS OF VENT GAS OF A UREA PLANT

PRIORITY CLAIM

This application is a national stage application of PCT/IB2017/055658, filed on Sep. 19, 2017, which claims the benefit of and priority to Italian Patent Application No. 102016000093986, filed on Sep. 19, 2016, the entire contents of which are each incorporated by reference herein.

TECHNICAL FIELD

The present disclosure relates to a system and a method for analysis of vent gas of a urea plant, as well as a urea plant equipped with a system for analysis of vent gas.

BACKGROUND

As is known, urea is produced on an industrial scale via processes based on the reaction, under relatively high-temperature and relatively high-pressure conditions, between carbon dioxide and ammonia to form ammonium carbamate, and the subsequent decomposition reaction of the ammonium carbamate to provide urea and water.

These processes are carried out in plants (urea plants) that generally comprise: a synthesis reactor, in which the reaction between carbon dioxide and ammonia takes place; purification and recovery sections, in which the aqueous urea solution produced in the reactor is progressively concentrated, with the recovery and recycling of unconverted reagents; and a finishing section, where the urea is solidified (for example, in a granulator or prilling tower).

However the urea plant is configured, the urea plant generates continuous vent gas, containing inert unconverted substances and also small quantities of unreacted ammonia. Depending on the process used in the urea plant, this vent gas may also contain oxygen, introduced for passivation in particular.

For example, a urea plant that adopts the technology known as "Snamprogetti" discharges, more specifically from a so-called medium-pressure recovery section, a continuous gas stream typically containing nitrogen, oxygen, argon, methane, ammonia, hydrogen and water.

The need arises to monitor vent gas of the urea plant, especially when this vent gas contains hydrogen and oxygen, in particular for meeting safety requirements and, specifically, for remaining outside of the ignition limits.

If a risk situation is detected, action is taken on the vent gas stream, for example, by adding steam or another control fluid (inert gas, natural gas or the like) so as to avoid the formation of an explosive mixture.

It is also necessary to check when the risk situation has passed, so as to interrupt injection of the control fluid (steam or the like) in safe conditions.

The use of a gas chromatograph has been proposed for the analysis, with the plant running, of a vent gas stream coming from a urea plant and containing ammonia.

Gas chromatographic analysis is often used for monitoring processes as it enables identifying and quantifying a relatively large number of components simultaneously. The individual sample components pass through a column at different speeds and are registered in succession by a detector. The time lapsing between introduction of the sample and the registration of a substance by the detector (retention time) is characteristic of the substance and is used to identify it. The magnitude of the detector signal is a measurement of the volumetric concentration of the component in the analysed fluid.

However, the use of a gas chromatograph has some drawbacks in the specific application of urea plant vent gas analysis.

First of all, the presence of condensing steam or another control fluid in the gas stream to be analysed (a situation that occurs following injection of steam or another fluid to move outside the ignition limits) undermines the gas chromatography measurement of the gas mixture's components, especially the quantitative analysis of ammonia.

Furthermore, the phenomena associated with the condensation-evaporation of steam (or any other fluids) in the gas chromatograph can compromise the mechanical integrity of the instrument.

In addition, a gas chromatograph is a relatively bulky instrument, also because it must be conditioned, and so, in general, a gas chromatograph cannot be placed directly on the main pipe in which the gas stream to be analysed circulates, but must be placed in a suitable structure in a remote position and be connected to the main pipe by a specially provided line, which can also be relatively long. All of this, apart from complicating the installation of the equipment, can also compromise measurement accuracy.

SUMMARY

One feature of the present disclosure is to provide a system and method for analysis of vent gas of a urea plant that enables overcoming certain of the above-mentioned drawbacks of certain of the known art.

In particular, one object of the disclosure is to provide a system and method for analysis of vent gas of a urea plant that enables relatively quick, relatively accurate and relatively reliable vent gas analysis in all operating conditions of the urea plant, even in the event of significant variations due, for example, to the injection of steam or another control fluid into the vent gas.

In accordance with the disclosure, a spectroscopic analysis technique is used for the analysis of vent gas of the urea plant, in particular Raman spectroscopy.

Raman spectroscopy is an analytical technique based on the vibrational and rotational energy of molecules and enables uniquely identifying the chemical species present in a sample and their relative amounts.

In Raman spectroscopy, a sample to be analysed is exposed to monochromatic electromagnetic radiation, typically emitted by a laser source, and the frequencies in the radiation scattered by the sample are detected and analysed.

By interacting with the electron molecules of the sample, the electromagnetic radiation induces variations in the vibrational and rotational energy of the molecules, with consequent scattering of the incident radiation. By analysing the scattered radiation, it is possible to identify components with different energy levels.

Raman spectroscopy analysis is performed by special instruments (Raman spectroscopes).

To date, this analytical technique does not appear to have ever been used in urea plants, in particular for the analysis of vent gas at risk of generating explosive mixtures, due to the structural limits of Raman spectroscopes, which are intrinsically unsuited for the purpose. Specifically, the following problems related to using Raman spectroscopes in urea plants have been identified:

a) the optical fibre probes that equip Raman spectroscopes have relatively low design temperatures (indicatively about 80° C.), and so the instruments cannot be supplied with samples at higher temperatures, which would cause mechanical damage upon contact with the probes. The vent gas of the urea plant to be analysed has, especially following the injection of steam or the like for restoring non-ignition conditions, temperatures decidedly higher than the damage threshold of the probes of Raman spectroscopes;

b) the vent gas of the urea plant to be analysed contains condensing water that carried ammonia with it: the condensable ammonia species is therefore present in the gas stream to be analysed, which can be absorbed by water and precipitate again in the main gas stream of the process. In consequence, the sample analysed by the Raman spectroscope would be affected by the quantitative precipitation of one of the components to be analysed, undermining the accuracy of the measurement.

The disclosure makes it possible to analyse, with the plant running and even substantially continuously or with a high sampling frequency, the vent gas at risk of forming explosive mixtures in a urea plant.

The analysis is carried out by a Raman spectroscope, opportunely engineered and installed in such a way as to provide reliable results, even in the event of deviations from the normal running conditions of the urea plant, for example, following injection of steam (or another control fluid) into the gas stream to be analysed to avoid the formation of possibly explosive mixtures.

In accordance with the disclosure, the Raman spectroscope is associated with a sampling interface positioned upstream of the Raman spectroscope and provided with a temperature control system.

The disclosure enables achieving the following main features:

analysis results, both qualitative and quantitative, which are relatively accurate and relatively reliable in any operating condition, even in the case of injecting steam or another control fluid into the gas stream to be analysed: the measurements, taken by the Raman spectroscope, are unaffected by the content of steam or another control fluid, as they are based on the atomic/steric properties of the chemical species and not their thermodynamic behaviour, as instead happens in gas chromatographic analysis;

in general, analysis is possible with the plant running, guaranteeing measurement accuracy and mechanical integrity of the instrument even in the presence of deviations from the normal operating conditions of the plant and/or deviations in pressure, temperature and relative content of the chemical species;

with respect to measurements taken with a gas chromatograph, response times are relatively quicker, measurements are more accurate and maintenance is relatively less expensive; and the Raman spectroscope is placed directly on the main pipe in which gas stream to be analysed circulates, and to which it is connected by a simple branch; auxiliary piping configured to carry the gas stream to be analysed to a remote position is not needed.

Additional features are described in, and will be apparent from the following Detailed Description and the figures.

BRIEF DESCRIPTION OF THE DRAWINGS

Further characteristics and advantages of the present disclosure will become clearer from the description of the following non-limitative embodiments, referring to the figures in the accompanying drawings, in which.

DETAILED DESCRIPTION

Figure 1:
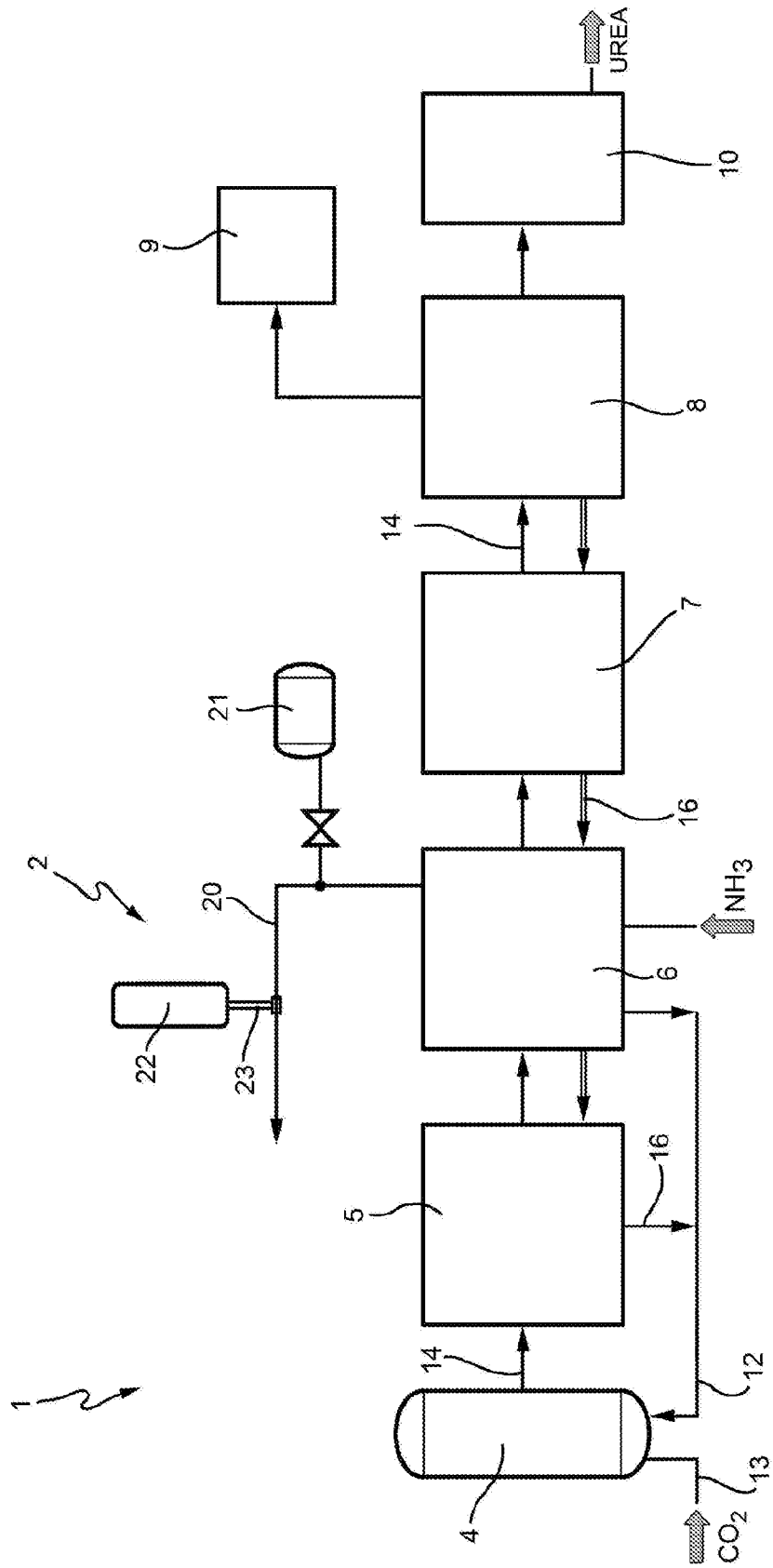
FIG. 1 is a schematic view of a urea production plant equipped with a system for analysis of vent gas in accordance with the disclosure.
Figure 2:
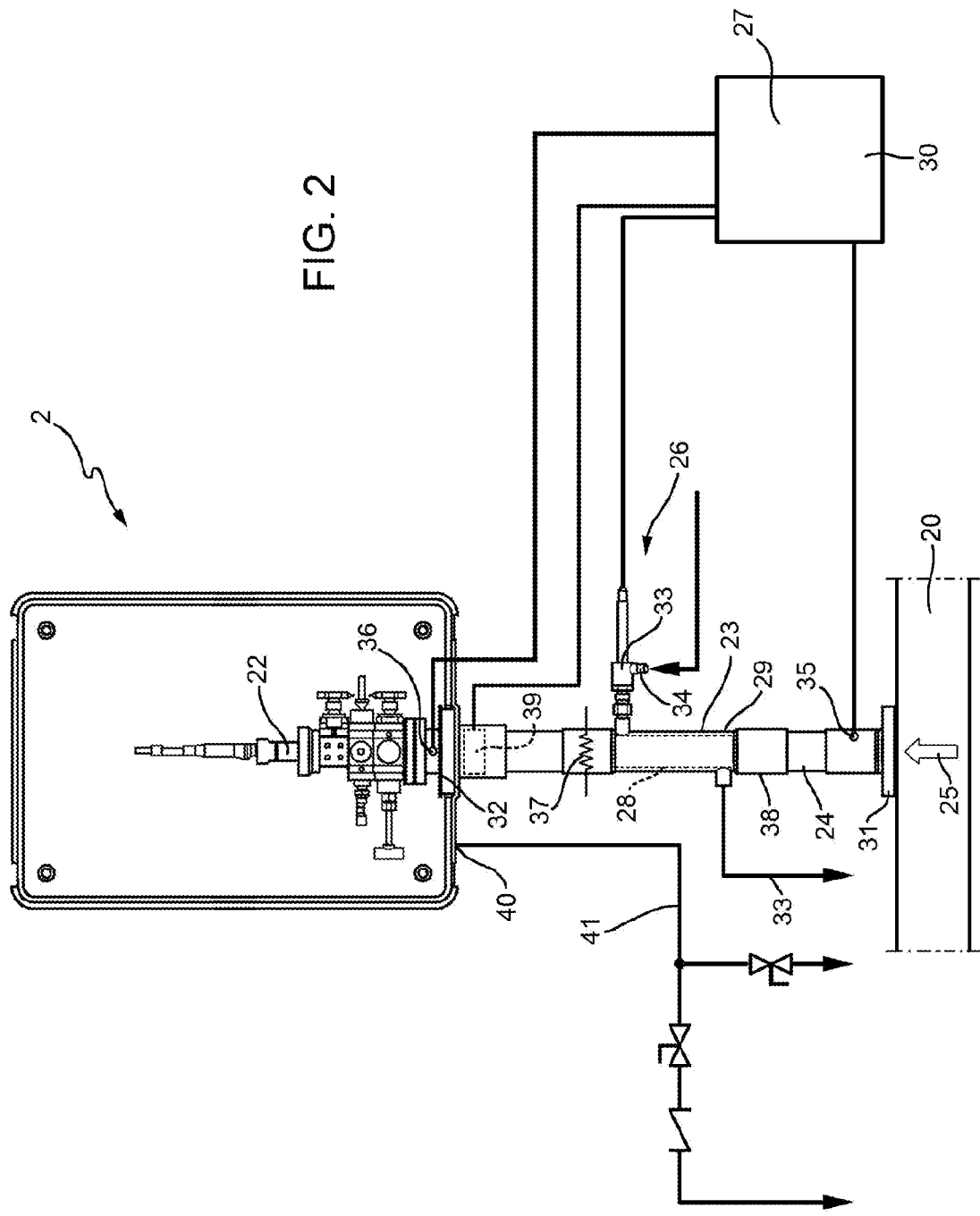
FIG. 2 is a schematic view of a system for analysis of vent gas of a urea plant in accordance with the disclosure.

Referring now to the example embodiments of the present disclosure illustrated in FIGS. 1 to 2 and specifically with reference to FIG. 1 which shows, in a purely schematic and simplified manner, a urea plant 1, or rather a plant for the production of urea, equipped with a system 2 for analysis of vent gas produced in the urea plant 1.

The urea plant 1, as well as the urea production process implemented therein, can be one of several types.

Here, reference is made, purely by way of example, to a urea production plant/process according to the known "Snamprogetti" technology. It remains understood that the disclosure is also applicable to other urea production plants/processes.

In the non-limitative configuration shown, but not necessarily, the urea plant 1 comprises: a urea synthesis reactor 4, where the reaction of urea synthesis from ammonia and carbon dioxide takes place; recovery sections 5, 6 and 7, in particular a high-pressure recovery section 5, a medium-pressure recovery section 6 and a low-pressure recovery section 7, where a urea solution produced in the reactor 4 is progressively concentrated by the removal of unreacted ammonia and carbon dioxide and water, and the recovered components are recirculated; a vacuum concentration section 8, connected to a treatment section 9 for process condensates (e.g., water); and a finishing/solidification section 10, comprising, for example, in a granulator or prilling tower.

The reactor 4 is fed with NH3 and CO2 through respective feed lines 12 and 13. A main urea line 14 connects a product outlet of the reactor 4 to the recovery sections 5, 6 and 7 and to the concentration section 8.

A recovery circuit 16 connects the recovery sections 5, 6 and 7 and the concentration section 8 to each other and to the NH3 feed line 12 configured to recirculate the unreacted components recovered by the recovery sections 5, 6 and 7 to the reactor 4.

For example, but not necessarily, the main urea line 14 connects in series (by respective line segments): the reactor 4, where the urea synthesis reaction from ammonia and carbon dioxide takes place; a stripper of the high-pressure recovery section 5, where unconverted NH3 and CO2 and ammonium carbamate are recovered and recycled to the reactor 4 through the recovery circuit 16; a medium-pressure decomposer in the medium-pressure recovery section 6 and a low-pressure decomposer in the low-pressure recovery section 7, in which the carbamate is decomposed to give NH3 and CO2, which are recycled to the reactor 4 through the recovery circuit 16; and one or more exchangers/concentrators in the concentration section 8, where the urea solution leaving the low-pressure recovery section 7 is concentrated before being sent to a granulator or prilling tower of the finishing/solidification section 10 for being granulated or prilled.

As the components of the various sections and the connection lines between them are generally known, the components of the various sections and the connection lines between them will not be shown nor described in detail herein.

In the urea plant 1, in particular in the recovery sections 5, 6 and 7 and in the concentration section 8, vent gas also containing ammonia is produced. The system 2 is connected to the urea plant 1 to receive and analyse at least one stream of vent gas produced in the urea plant 1.

In the non-limitative example shown, but not necessarily, the system 2 receives and analyses vent gas coming from the medium-pressure recovery section 6 and, in particular, that leaving the medium-pressure decomposer and conveyed in a main pipe 20.

As, among other things, this vent gas contains hydrogen and oxygen, explosive mixtures may form, and so the main pipe 20 is connected to an injection device 21 configured to inject a control fluid, for example, steam or another fluid, operated (manually by an operator via a control in the control room, or automatically by a control unit) when the system 2 detects potentially hazardous conditions for the formation of explosive mixtures.

It remains understood that the system 2 can be used for analysing other effluents and/or gas streams produced in the urea plant 1 (which, as already pointed out, can also have a different configuration from that shown herein by way of example). The system 2 can therefore be placed in a different position from that described and shown herein by way of example, as well as in a different type of urea plant.

Referring to FIG. 2 as well, the system 2 comprises a Raman spectroscope 22 and a sampling interface 23 that connects the spectroscope 22 to the main pipe 20 in which the vent gas to be analysed circulates. The spectroscope 22 comprises: at least one source of electromagnetic radiation, in particular a laser source, which directs monochromatic electromagnetic radiation on the sample to be analysed in an analysis chamber; at least one probe, in particular an optical fibre probe, which receives radiation scattered by the sample; and an analyser that analyses the frequencies present in the radiation scattered by the sample. As the spectroscope 22 is generally known, the spectroscope 22 will not be shown nor described in detail herein.

A feature of the present disclosure is that the spectroscope 22 is placed above the main pipe 20.

The sampling interface 23 comprises a sampling conduit 24, which connects the main pipe 20 to the spectroscope 22 to convey a continuous sample gas stream 25 from the main pipe 20 to the spectroscope 22; a temperature-adjusting device 26, controlled by a temperature controller 27 and acting on at least one thermal treatment portion 28 of the conduit 24 to adjust the temperature of the sample stream 25 circulating in the conduit 24; a reflux device 29 to return a condensate fraction of the sample stream 25, which has condensed following a cooling of the sample stream 25 in portion 28, back into the main pipe 20; and a processing and control unit 30 configured so as to calculate the amount of condensable species returned to the main pipe 20.

The conduit 24 connects the main pipe 20 to the spectroscope 22; in particular, the conduit 24 is connected to a connector 31 fitted on the main pipe 20 and to an inlet 32 of the spectroscope 22 and, more precisely, to the analysis chamber of the spectroscope 22.

Another feature of the present disclosure is that the conduit 24 departs vertically from the main pipe 20, and/or extends substantially vertically or slanting upwards from the connector 31.

The temperature-adjusting device 26 can be of one of several types. In general, the device 26 is configured to reduce the temperature of the sample stream 25 when the temperature is too high and could damage the components of the spectroscope 22, in particular its optical fibre probe. For example, the device 26 comprises: a cooling circuit 33, arranged around portion 28 of the conduit 24 and in which a cooling fluid circulates (for example, air or water); and at least one circulation member 34 controlled by the temperature controller 27 and configured to circulate the cooling fluid in the cooling circuit 33.

The temperature controller 27 (which can also be integrated in the processing and control unit 30 of the spectroscope 22) is, in certain embodiments, of the so-called "dual-loop" type and is connected to a pair of temperature sensors 35 and 36, respectively positioned upstream and downstream of portion 28 of the conduit 24 in the circulation direction of the sample stream 25 in the conduit 24 (for example, the temperature sensors 35 and 36 are arranged at an inlet of the conduit 24 and the inlet 32 of the spectroscope 22, respectively), to detect the temperature of the gas stream coming from the urea plant 1 through the main pipe 20 and of the sample stream 25 analysed in the spectroscope 22, respectively.

In particular, the temperature controller 27 is a controller of the proportional-integral-derivative type.

The temperature controller 27 is set to a temperature (for example, 70° C.) lower than a threshold temperature at which the components of the spectroscope 22 could become damaged (in particular, the optical fibre probe or probes).

Another feature of the present disclosure is that the device 26 also comprises a heating element 37, for example an electric resistance, positioned in the conduit 24 downstream (always referring to the circulation direction of the sample stream 25) of portion 28 and of the cooling circuit 33, and in turn operated by the temperature controller 27 and/or by the processing and control unit 30 to raise the temperature (by a few degrees, indicatively 1-5° C.) of the sample stream 25 after the cooling induced by the cooling circuit 33, to ward off saturation conditions of the sample stream 25 entering the spectroscope 22.

The cooling induced by the device 26 may cause the condensation of chemical species in the sample stream 25. The condensate fraction flows back into the main pipe 20 through the reflux device 29. For example, the reflux device 29 comprises a collecting portion 38 of the conduit 24; the portion 38 is placed above the main pipe 20 and beneath the thermal treatment portion 28 of the conduit 24 and is substantially vertical or slanted towards the main pipe 20 so that the condensate fraction falls through portion 38 into the main pipe 20 below, due to the effect of gravity.

The processing and control unit 30 is configured so as to calculate the amount of condensable species that are recirculated to the main pipe 20, via opportune computation algorithms based on thermodynamic models of the process implemented in the urea plant 1 and on the operating parameters of this process.

Optionally, the system also includes an automatic emergency shut-off valve 39, placed at the inlet 32 of the spectroscope 22 or along the conduit 24, to interrupt the supply of the sample stream 25 to the spectroscope 22 in the event of failure/malfunctioning of the temperature controller 27; the valve 39 intervenes automatically following any uncontrolled heat increase (above a preset danger threshold) to protect the spectroscope 22.

The spectroscope 22, or more specifically its analysis chamber, has an outlet 40 that is connected to the return conduit 41; the return conduit 41 is connected to the main pipe 20 and, in particular, is fitted on the main pipe 20 downstream of the connector 31 in the circulation direction of the vent gas circulating in the main pipe 20, to return the sample stream 25 that transited through the spectroscope 22 back to the main pipe 20.

In use, a gas stream constituted by vent gas produced in the urea plant 1 circulates in the main pipe 20.

The gas stream contains, purely by way of example, nitrogen, oxygen, argon, methane, ammonia, hydrogen and water, and has a temperature of approximately 50° C.-170° C.

Part of the gas stream circulates through the conduit 24 and constitutes the sample stream 25 sent, in certain embodiments continuously, to the spectroscope 22.

If the temperature of the sample stream 25 is lower than a preset temperature threshold (as in normal operating conditions of the urea plant 1), the temperature controller 27 does not operate the temperature-adjusting device 26 and the sample stream 25 reaches the spectroscope 22.

The spectroscope 22 performs qualitative and quantitative analysis on the sample stream 25.

If the analysis detects conditions for the possible formation of explosive mixtures, the system 2 generates an alarm signal, on the basis of which the injection device 21 is (manually or automatically) activated for injecting steam (indicatively at 200° C.-250° C.) or another control fluid into the gas stream circulating in the main pipe 20.

The injection of steam or another control fluid raises the temperature of the gas stream, and therefore also that of the sample stream 25, as well as varying its composition, but the system 2 is configured to effectively and correctly operate also in changed conditions.

In these embodiments, if the temperature controller 27 detects, via the temperature sensors 35 and 36, a temperature of the sample stream 25 above the threshold temperature, the temperature controller 27 operates the temperature-adjusting device 26 to cool the sample stream 25 and bring the temperature of the sample stream 25 back below the threshold temperature.

Opportunely, the device 26 then intervenes, via the heating element 37, to slightly heat (a few degrees, indicatively 1° C.-5° C.) the previously cooled sample stream 25 (in any case, keeping the temperature below the threshold temperature), to ward off saturation conditions of sample stream 25.

Any condensate fraction of the sample stream 25 falls back into the main pipe 20 through the reflux device 29.

The system 2 analyses the sample stream 25. The spectroscope 22 takes measurements at predetermined time intervals, or operates substantially continuously, depending on the measurement and response times of the instrument; the sample stream 25, after having travelled through the conduit 24 and reached the spectroscope 22, returns to the main pipe 20 through the return conduit 41, more specifically (in certain embodiments) downstream, in the direction of circulation of the vent gas circulating in the main pipe 20, of the connector 31, or rather of the sampling point where the sample stream 25 is taken from the main pipe 20 and sent to the spectroscope 22.

When the system 2 detects that the conditions of possible formation of explosive mixtures have ceased, the system 2 generates an all-clear signal, on the basis of which injection of the control fluid (steam or the like) into the main pipe 20 is (manually or automatically) interrupted.

Finally, it is understood that further modifications and variants can be made regarding the system and method for analysis of vent gas of a urea plant and the urea plant described and illustrated herein without departing from the scope of the appended claims. As such, the present disclosure also covers embodiments not described in the detailed description and equivalent embodiments that fall within scope of the appended claims. Accordingly, various changes and modifications to the presently disclosed embodiments will be apparent to those skilled in the art. Such changes and modifications can be made without departing from the spirit and scope of the present subject matter and without diminishing its intended technical scope. It is therefore intended that such changes and modifications be covered by the appended claims.

The invention claimed is:

1. A urea plant vent gas analysis system comprising:
a Raman spectroscope;
a sampling conduit having a connector connectable to a main pipe of a urea plant and configured to convey a sample stream of gas from the main pipe to the Raman spectroscope;
a temperature-adjusting device, operated by a temperature controller and configured to act on a thermal treatment portion of the sampling conduit to adjust a temperature of the sample stream circulating in the sampling conduit, wherein the temperature controller is set to a temperature lower than a threshold temperature that can damage components of the Raman spectroscope and the temperature-adjusting device comprises:
a cooling circuit arranged around the thermal treatment portion of the sampling conduit and in which a cooling fluid circulates,
a circulation member controllable by the temperature controller and configured to circulate the cooling fluid in the cooling circuit, and
a heating element positioned in the sampling conduit downstream, in a circulation direction of the sample stream in the sampling conduit, of the thermal treatment portion and of the cooling circuit, the temperature controller configured to cause the heating element to raise the temperature of the sample stream after the cooling of the sample stream caused by the cooling circuit to ward off saturation conditions of the sample stream entering the Raman spectroscope; and
a reflux device configured to collect and return to the main pipe a condensate fraction of the sample stream that is condensed following a cooling of the sample stream in the thermal treatment portion of the sampling conduit.

2. The urea plant vent gas analysis system of claim 1, further comprising a processing and control unit configured to calculate an amount of condensable species returned to the main pipe.

3. The urea plant vent gas analysis system of claim 1, wherein the reflux device comprises a collecting portion of the sampling conduit, the collecting portion being positioned above the main pipe and beneath the thermal treatment portion of the sampling conduit, the collecting portion being positioned such that the condensate fraction falls, based on gravity, through the collecting portion and into the main pipe.

4. The urea plant vent gas analysis system of claim 3, wherein the collecting portion is one of: vertically positioned and slantedly positioned toward the connector.

5. The urea plant vent gas analysis system of claim 1, wherein the Raman spectroscope is positioned above the main pipe of the urea plant and the sampling conduit is in a position selected from the group consisting of: vertically departing from the main pipe, vertically extending from the connector, and slantedly upwards extending from the connector.

6. The urea plant vent gas analysis system of claim 1, wherein the temperature controller comprises a dual-loop type controller and is connected to a first temperature sensor positioned upstream in a circulation direction of the sample stream in the sampling conduit, and a second temperature sensor positioned downstream in the circulation direction of the sample stream in the sampling conduit.

7. The urea plant vent gas analysis system of claim 1, further comprising an automatic emergency shut-off valve configured to interrupt a supply of the sample stream to the Raman spectroscope if the temperature of the sample stream rises above a preset danger threshold temperature, the automatic emergency shut-off valve positioned at one of: an inlet of the Raman spectroscope and along the sampling conduit.

8. The urea plant vent gas analysis system of claim 1, wherein the Raman spectroscope has an outlet connected to a return conduit that is connectable to the main pipe, the outlet being configured to return the sample stream conveyed through the Raman spectroscope back to the main pipe downstream, in a vent gas circulation direction through the main pipe, of the connector.

9. The urea plant vent gas analysis system of claim 1, wherein the sampling conduit conveys a continuous sample stream of gas from the main pipe to the Raman spectroscope.

10. A urea plant comprising:
 a main pipe; and
 a urea plant vent gas analysis system comprising:
  a Raman spectroscope;
  a sampling conduit having a connector connectable to the main pipe and configured to convey a sample stream of gas from the main pipe to the Raman spectroscope;
  a temperature-adjusting device, operated by a temperature controller and configured to act on a thermal treatment portion of the sampling conduit to adjust a temperature of the sample stream circulating in the sampling conduit, wherein the temperature controller is set to a temperature lower than a threshold temperature that can damage components of the Raman spectroscope and the temperature-adjusting device comprises:
   a cooling circuit arranged around the thermal treatment portion of the sampling conduit and in which a cooling fluid circulates,
   a circulation member controllable by the temperature controller and configured to circulate the cooling fluid in the cooling circuit, and
   a heating element positioned in the sampling conduit downstream, in a circulation direction of the sample stream in the sampling conduit, of the thermal treatment portion and of the cooling circuit, the temperature controller configured to cause the heating element to raise the temperature of the sample stream after the cooling of the sample stream caused by the cooling circuit to ward off saturation conditions of the sample stream entering the Raman spectroscope; and
  a reflux device configured to collect and return to the main pipe a condensate fraction of the sample stream that is condensed following a cooling of the sample stream in the thermal treatment portion of the sampling conduit.

11. A method for analyzing vent gas of a urea plant, the method comprising:
 taking a sample stream of gas from a main pipe of the urea plant for analysis by Raman spectroscopy performed in a Raman spectroscope; and
 controlling a temperature of the sample stream to maintain the temperature below a preset threshold temperature that can damage components of the Raman spectroscope, the controlling of the temperature of the sample stream including:
  detecting the temperature of the sample stream in a sampling conduit that conveys the sample stream to the Raman spectroscope,
  responsive to the detected temperature being higher than the preset threshold temperature:
   cooling, via a cooling circuit in which a cooling fluid circulates, the sample stream,
   thereafter, heating, via a heating element, the sample stream to raise the temperature of the sample stream to ward off saturation conditions of the sample stream entering the Raman spectroscope,
   collecting a condensate fraction of the sample stream condensed in the cooling of the sample stream, and
  returning said condensate fraction back to the main pipe.

12. The method of claim 11, wherein detecting the temperature of the sample stream comprises detecting the temperature upstream and downstream, in a circulation direction of the sample stream in the sampling conduit, of a thermal treatment portion of the sampling conduit in which the sample stream is cooled.

13. The method of claim 11, further comprising calculating an amount of condensable species brought back into the main pipe.

14. The method of claim 11, wherein the Raman spectroscope is positioned above the main pipe and connected to the main pipe via a sampling conduit which is in a position selected from the group consisting of: vertically departing from the main pipe, vertically extending from a connector joining the sampling conduit to the main pipe, and slantedly upwards extending from the connector.

15. The method of claim 11, further comprising interrupting a supply of the sample stream to if the temperature of the sample stream of gas rises above a preset danger threshold temperature.

16. The method of claim 11, further comprising returning the sample stream analysed by Raman spectroscopy back into the main pipe downstream, in a vent gas circulation direction through the main pipe, of a sampling point in which the sample stream of gas is taken from the main pipe.

* * * * *